(12) United States Patent
Kigoshi et al.

(10) Patent No.: US 6,254,889 B1
(45) Date of Patent: *Jul. 3, 2001

(54) SOLID DISPERSION DOSAGE FORM OF AMORPHOUS XANTHINE DERIVATIVE AND ENTERIC-COATING POLYMER

(75) Inventors: Makoto Kigoshi, Shizuoka; Tomoaki Masada; Yasuhiko Ueno, both of Mishima; Yasuhiro Ishikawa, Shizuoka; Eiji Hayakawa, Susono, all of (JP)

(73) Assignee: Kyowa Hakko Kogyo Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/809,651

(22) PCT Filed: Jun. 7, 1996

(86) PCT No.: PCT/JP96/01555

§ 371 Date: Mar. 26, 1997

§ 102(e) Date: Mar. 26, 1997

(87) PCT Pub. No.: WO97/04782

PCT Pub. Date: Feb. 13, 1997

(30) Foreign Application Priority Data

Jul. 26, 1995 (JP) ................................... 7-190058

(51) Int. Cl.[7] .............. A61K 9/10; A61K 9/14; A61K 9/22; A61K 9/52
(52) U.S. Cl. ............ 424/487; 424/488; 424/499; 424/501; 424/494; 424/497; 424/457; 424/468
(58) Field of Search .............. 424/484, 486–488, 424/494, 496, 499, 501, 457, 468; 514/960, 964

(56) References Cited

U.S. PATENT DOCUMENTS 3,976,071 * 8/1976 Sadek .
4,921,707 * 5/1990 Racz et al. .
5,028,664 * 7/1991 Ohmura et al. .
5,286,489 * 2/1994 Tsam et al. .
5,290,782   3/1994 Suzuki et al. ..................... 514/263
5,456,923 * 10/1995 Nakamichi et al. .

FOREIGN PATENT DOCUMENTS 63-222116   9/1988 (JP) .

OTHER PUBLICATIONS

*Chemical & Pharmaceutical Bulletin*, vol. 42, No. 2 (1994), pp. 354–358.
*STP Pharma Sciences*, vol. 2, No. (1992), pp. 186–192.
*Pharmacia*, vol. 32 (1977), pp. 511–515.

* cited by examiner

Primary Examiner—Edward J. Webman
(74) Attorney, Agent, or Firm—Fitzpatrick, Cella, Harper & Scinto (57) ABSTRACT

The present invention relates to a solid dispersion and a solid dispersion dosage form which comprise a xanthine derivative represented by the following formula (I) or a pharmacologically allowable salt thereof and a polymer.

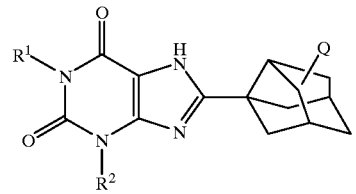

(I)

(In the above formula, $R^1$ and $R^2$ are the same or different, and represent substituted or unsubstituted lower alkyl groups, and Q represents a hydrogen atom or a hydroxyl group.)

4 Claims, 3 Drawing Sheets

SOLID DISPERSION DOSAGE FORM OF AMORPHOUS XANTHINE DERIVATIVE AND ENTERIC-COATING POLYMER

TECHNICAL FIELD

The present invention relates to a solid dispersion and a solid dispersion dosage form of a xanthine derivative or a pharmacologically allowable salt thereof which exhibits an antagonistic activity relative to the adenosine A1 receptor, and which has a diuretic activity, a kidney-protecting activity, a bronchodilating activity, a cerebral function-improving activity, an anti-dementia activity, or the like.

BACKGROUND ART

In general, drugs which are slightly soluble in water and have high crystallinity have low bioavailability since they have low solubility and low disolution rate in the gastrointestinal tract. Hitherto, in order to improve their absorbability, several methods for finely grinding drug crystals or for transforming them into amorphous substances have been examined.

By fine-grinding, however, particle diameters become irregular between lots, or inter-particle force is enhanced to cause agglomeration.

As a method for obtaining amorphous substances, grinding or forming a solid dispersion are considered. Drug crystals which can become amorphous by grinding are limited. Further, it has been known that solubility and absorbability of a slightly water-soluble compound are improved by dispersing it in a polymer to form a solid dispersion.

As to xanthine derivatives or pharmacologically allowable salts thereof, which are slightly soluble, however, solid dispersions or solid dispersion dosage forms are not yet known.

DISCLOSURE OF THE INVENTION

The present invention relates to a solid dispersion comprising a xanthine derivative or a pharmacologically allowable salt thereof and a polymer, the xanthine derivative [hereinafter referred to as compound (I)] being represented by the following formula (I).

(I)

(In the above formula, $R^1$ and $R^2$ are the same or different, and represent substituted or unsubstituted lower alkyl groups, and Q represents a hydrogen atom or a hydroxyl group.)

Furthermore, the present invention relates to a solid dispersion dosage form comprising a xanthine derivative of a compound (I) or a pharmacologically allowable salt thereof and a polymer.

In the definition of the formula (I), the lower alkyl groups are straight or branched groups having 1 to 6 carbon atoms, and examples include a methyl group, an ethyl group, a propyl group, an isopropyl group, a butyl group, an isobutyl group, a sec-butyl group, a tert-butyl group, a pentyl group, a neopentyl group, and a hexyl group. As to substituent groups of the substituted lower alkyl groups, examples include a hydroxyl group and an acetyl group.

The pharmacologically allowable salts of compounds (I) include pharmacologically allowable acid addition salts, metal salts, ammonium salts, organic amine addition salts, and amino acid addition salts.

Examples of pharmacologically allowable acid addition salts of compounds (I) include inorganic acid salts such as hydrochlorides, sulfates, phosphates; and organic acid salts such as acetates, maleates, fumarates, tartrates, and citrates. Examples of pharmacologically allowable metal salts include alkali metal salts such as lithium salts, sodium salts, and potassium salts; alkaline earth metal salts such as magnesium salts and calcium salts; aluminum salts; and zinc salts. Examples of pharmacologically allowable ammonium salts include salts of ammonium or tetramethyl ammonium. Examples of pharmacologically allowable organic amine addition salts include addition salts of morpholine or piperidine. Examples of pharmacologically allowable amino acid addition salts include addition salts of lysine, glycine, phenylalanine, glutamic acid, and aspartic acid.

Compounds (I) or pharmacologically allowable salts thereof can be produced according to the method described in Japanese Unexamined Patent Publication No. 3-173889.

Practical examples of compounds (I) are shown in Table 1.

TABLE 1

| Compound No. | $R^1$ | $R^2$ | X |
|---|---|---|---|
| 1 | n-$C_3H_7$ | n-$C_3H_7$ | |
| 2 | n-$C_3H_7$ | n-$C_3H_7$ | OH |
| 3 | n-$C_3H_7$ | n-$C_3H_7$ | OH |
| 4 | $CH_3CHCH_2$<br>\|<br>OH | n-$C_3H_7$ | OH |

TABLE 1-continued

| Compound No. | R¹ | R² | X |
|---|---|---|---|
| 5 | CH₃CCH₂ (with =O) | n-C₃H₇ | (bicyclic structure with OH) |

In the solid dispersion or the solid dispersion dosage form, a compound (I) or a pharmacologically allowable salt thereof is contained at 1 to 50% by weight, and preferably, 3 to 10% by weight.

The polymer to be used in the present invention is not particularly limited so long as it can disperse compounds (I) or pharmacologically allowable salts thereof, and accordingly, several natural polymers and synthetic polymers can be used. Examples of polymers include rubber compounds such as gum arabic; gelatin; polysaccharides such as agar; cellulose compounds or derivatives thereof such as crystalline cellulose, micro crystalline cellulose, low-substituted hydroxypropyl cellulose, carboxymethyl cellulose, hydroxypropylmethyl cellulose, hydroxypropylmethyl cellulose phthalate, hydroxypropylmethyl cellulose acetate succinate, carboxymethyl ethyl cellulose, ethyl cellulose, and cellulose acetate phthalate; polyvinyl derivatives such as polyvinyl alcohol, polyvinyl pyrrolidone, and polyvinyl acetal diethylaminoacetate; aminoalkyl methacrylate copolymers such as aminoalkyl methacrylate copolymer E and aminoalkyl methacrylate copolymer RS; and methacrylate copolymers such as methacrylate copolymer L, methacrylate copolymer LD, and methacrylate copolymer S. Among these polymers, enteric-coating polymers are preferred. Examples of enteric-coating polymers include methacrylate copolymer L (trade name: Eudragit L100 and Eudragit L100-55; Röhm Pharma Co., Ltd.), hydroxypropylmethyl cellulose phthalate (trade name: hydroxypropylmethyl cellulose phthalate HP-55; Shin-Etsu Chemical Co., Ltd.), hydroxypropylmethyl cellulose acetate succinate, and carboxymethylethyl cellulose. Particularly, methacrylate copolymer L (trade name: Eudragit L100) is preferably used.

Such a polymer is contained in the solid dispersion or the solid dispersion dosage form at 3 to 50% by weight, and preferably, 9 to 10% by weight.

In the solid dispersion or the solid dispersion dosage form of the present invention, the blending ratio of a compound (I) to the polymer is 3:1 to 1:5 (by weight). In particular, when the content of a compound (I) or a pharmacologically allowable salt thereof is 3% by weight, the blending ratio is preferably 1:3, and when the content of a compound (I) or a pharmacologically allowable salt thereof is 10 to 20% by weight, the blending ratio is preferably 1:1.

The solid dispersion of the present invention can be prepared by a co-grinding method, a solvent method, a melting method, a heat-melt-kneading method, or the like.

In the co-grinding method, a compound (I) or a pharmacologically allowable salt thereof is mixed with a polymer using a mixer or the like, and the mixture is ground using a grinder or the like. In the solvent method, a compound (I) or a pharmacologically allowable salt thereof and a polymer are dissolved or dispersed in an organic solvent, and the organic solvent is then removed according to an ordinary method under reduced pressure or ordinary pressure.

The organic solvent to be used in the solvent method is not particularly limited so long as it can dissolve a compound (I) or a pharmacologically allowable salt thereof and a polymer. Examples of such organic solvents include aliphatic halogenated hydrocarbons, ketones, alcohols, ethers, aliphatic hydrocarbons, aromatic hydrocarbons, esters, organic acids, amides, and mixed solvents thereof. Examples of aliphatic halogenated hydrocarbons include methylene chloride, dichloroethane, and chloroform. Examples of ketones include acetone and methyl ethyl ketone. Examples of alcohols include methanol, ethanol, propanol, and butanol. Examples of ethers include diethyl ether, dibutyl ether, diisobutyl ether, dioxane, tetrahydrofuran, and ethylene glycol dimethyl ether. Examples of aliphatic hydrocarbons include n-hexane, cyclohexane, and n-heptane. Examples of aromatic hydrocarbons include benzene, toluene, and xylene. Examples of esters include ethyl acetate. Examples of organic acids include acetic acid and propionic acid. Examples of amides include dimethylformamide and dimethylacetamide. Aliphatic halogenated hydrocarbons, alcohols, and mixtures of aliphatic halogenated hydrocarbons and alcohols are preferably used, and an ethanol/methylene chloride (1/1) mixture is particularly preferably used.

As to removal of the organic solvent, operating conditions such as the treatment temperature and time period are ordinarily at room temperature to 150° C. and for several minutes to more than ten hours, though they are altered depending on the compound, the polymer, the solvent, or the like to be used.

According to the solvent method, the solid dispersion is produced using, for example, a fluidized-bed granulator, an agitating granulator, or a vacuum-dry granulator, and specifically, is produced as follows.

A compound (I) or a pharmacologically allowable salt thereof is dissolved in an organic solvent with a polymer to prepare a spray solution. At this point, a surfactant may be added to the spray solution. Examples of surfactants include sodium lauryl sulfate, polysolbate 80, and sucrose-fatty acid esters. Although there exist several sucrose-fatty acid esters having different HLB values which vary depending on the carbon chain of the fatty acid or the ester concentration, sucrose-fatty acid esters having high HLB values such as a sucrose-fatty acid ester having an HLB value of 22 (Ryoto-Sugar Ester DK-SS; Mitsubishi Chemical Corporation) are preferably used. The surfactant concentration is preferably 0.1 to 5.0% by weight.

In such a spray solution, the solid ingredient concentration based on the compound (I) or the pharmacologically allowable salt thereof and the polymer is 5 to 23% by weight/volume, preferably 11 to 15% by weight/volume, and more preferably 15% by weight/volume.

The solid dispersion dosage form of the present invention can be obtained by spray-drying such a spray solution or spraying it onto an absorbent carrier, or by injecting it into water and isolating the resulting granules. Excipients ordinarily used in the pharmaceutical field can be used as absorbent carriers. Examples of excipients include saccharides such as lactose, sucrose, glucose, reducing maltose, mannitol, and sorbitol; starch or derivatives thereof such as corn starch, potato starch, dextrin, and pullulane; cellulose compounds such as crystalline cellulose and micro crystalline cellulose; amino acids such as arginine, asparagine, aspartic acid, citrulline, cysteine, glutamic acid, glutamine, glycine, histidine, homoserine, isoleucine, leucine, lysine, methionine, ornithine, phenylalanine, proline, serine, threonine, tryptophan, tyrosine, valine; aminobutyric acid; aminocapronic acid; and glycylglycine. For example, among lactose products, those having a mesh size of #200 are particularly preferred.

For performing such spray-drying, a granulator may be used which is further equipped with a vacuum-drying unit or a microwave drying unit.

In the melting method, a compound (I) or a pharmacologically allowable salt thereof is melted or dispersed in a polymer, and then quenched. For melting or dispersing, for example, the mixture is heated above the melting point or softening point of the compound (I), the pharmacologically allowable salt thereof, or the polymer. In this case, additives such as plasticizers or the aforementioned surfactants can be added. Examples of plasticizers include triethyl citrate, polyethylene glycol, and triacetin.

According to the melting method, the solid dispersion is produced using, for example, an agitating granulator with a heating unit. The compound (I) or the pharmacologically allowable salt thereof and the polymer are physically mixed beforehand. To this mixture, the aforementioned plasticizers, surfactants, or the like may be added as occasion demands. Operating conditions such as the treatment temperature and time period are ordinarily at room temperature to 150° C. and for several minutes to more than ten hours, though these are altered depending on the compound, the polymer, concentrations or types of additives, or the like to be used. Subsequently, quenching is carried out to obtain the solid dispersion. The quenching temperature is –80° C. to room temperature.

In the heat-melt-kneading method, a solid dispersion is obtained by a mixing process under heat and compression using an extruder having a heating unit, for example, a biaxial extruder. Operating conditions such as the treatment temperature, pressure, and time period are ordinarily at room temperature to 150° C., under 10 to 200 kg/cm$^2$, and for several minutes to more than ten hours, though they are altered depending on the compound, the polymer, concentrations or types of additives, or the like to be used.

According to the heat-melt-kneading method, a solid dispersion is produced using, for example, a biaxial extruder, and is specifically produced as follows.

A compound (I) or a pharmacologically allowable salt thereof and a polymer, and optional additives as described above are physically mixed beforehand. This mixture is then fed at a powder feeding rate of 10 to 200 g/min. As to treatment conditions, the screw rotating speed is 50 to 300 r.p.m., the temperature is 20 to 200° C., and the pressure is 40 to 120 kg/cm$^2$. Thus, a solid dispersion having a plastic characteristic can be obtained. Solid dispersion powder can be obtained by grinding the solid dispersion using a grinder.

Solid dispersions of compounds (I) or pharmacologically allowable salts thereof obtained according to the co-grinding method, the solvent method, the melting method, the heat-melt-kneading method, or the like can be used as they are in the form of a powder or granular dosage form. Alternatively, they may be further transformed into solid dispersion dosage forms through a formulating process such as a mixing process, a granulating process, a tabletting process, an encapsulating process, and a coating process.

The mixing process is, for example, a process for mixing such a solid dispersion and other compound using a mixer or the like. The granulating process is, for example, a process for granulating such a solid dispersion using a granulating mixer or the like. The tabletting process is, for example, a process for making such a solid dispersion into tablets using a tabletting machine or the like. The encapsulating process is, for example, a process for packing such a solid dispersion in capsules using an encapsulating machine or the like. The coating process is, for example, a process for coating such a solid dispersion with a coating agent using a coating machine or the like.

Dosage forms obtained according to the above-described manner include parvule dosage forms, granular dosage forms, tablets, capsule dosage forms, or the like. Further, an additive such as a coloring agent, a corrigent, an excipient, a disintegrator, a lubricant, and a surfactant can be added as occasion demands. Such an additive can be added in a manner suitable for each process. Examples of coloring agents include yellow iron sesquioxide, iron sesquioxide, several food dyes, and copper sodium chlorophyllin. Examples of corrigents include sucrose, saccharin, aspartame, mannitol, dextran, a lemon flavor, menthol, and citric acid. Examples of excipients include the aforementioned excipients. Examples of disintegrators include hydroxypropyl cellulose, sodium croscarmellose, crospovidone, and sodium carboxymethyl starch. Examples of lubricants include magnesium stearate. Examples of surfactants include the aforementioned surfactants.

When an automatic encapsulating or tabletting machine is used, 0.5 to 2% by weight of magnesium stearate as a lubricant should preferably be mixed before the encapsulating or tabletting process in order to prevent powder adhesion onto the piston or punch.

Advantages of the solid dispersion or the solid dispersion dosage form according to the present invention will be illustrated with experimental examples.

EXPERIMENTAL EXAMPLE 1

Figure 1:
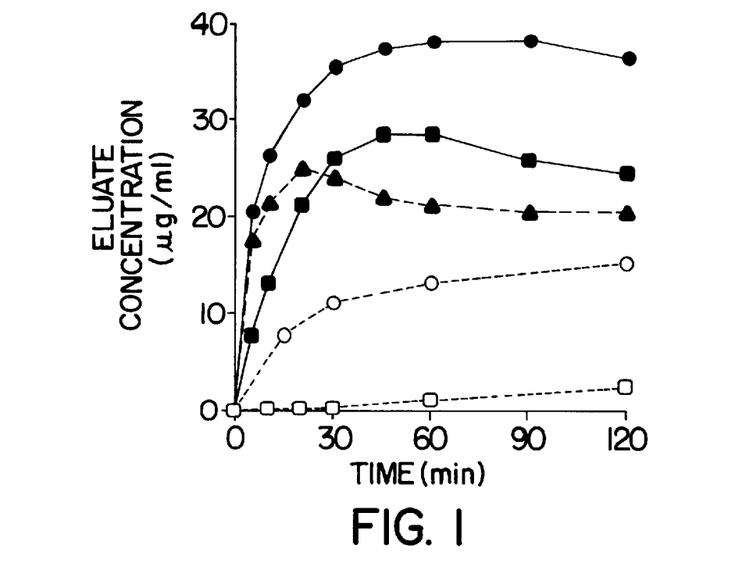
FIG. 1 shows the results of the dissolution tests for the solid dispersions of Examples 1 to 3, the crystal of Compound No. 1, and the dosage form of Comparative Example 1. The results for the dosage form of Example 1 are represented by black dots, those for the solid dispersion of Example 2 are represented by black squares, those for the solid dispersion of Example 3 are represented by black triangles, those for the crystal of Compound No. 1 are represented by white squares, and those for the dosage form of Comparative Example 1 are represented by white dots.

One point six seven gram of each of the solid dispersions obtained in Examples 1 and 3, and 0.50 g pf the solid dispersion obtained in Example 2 were each put in 900 ml of a solution containing 0.3% by weight of sodium lauryl sulfate in order to perform an dissolution test by a puddle method at 37° C. and 100 r.p.m. The results are shown in FIG. 1. For comparison, similar dissolution tests were performed using 50 mg of Compound No. 1 crystals and tablets obtained in Comparative Example 1 instead of the solid dispersion. The results are shown in FIG. 1. As is revealed in FIG. 1, the solubility of the solid dispersions according to the present invention was significantly higher than those of the Compound No. 1 crystal and the dosage form obtained in Comparative Example 1.

EXPERIMENTAL EXAMPLE 2

The solid dispersion dosage forms obtained in Examples 6, 7, and 8 were each orally administered to a male beagle with 20 ml of water. For comparison, dosage forms each comprising 5 mg of Compound No. 1 crystals packed in a gelatin hard capsule and tablets of Comparative Example 1 were administered to beagles in a similar manner. The dosage of each dosage form (the weight of Compound No. 1 per 1 kg body weight), and the number of dogs per group are shown in Table 2.

TABLE 2

|  | Dosage (mg/kg) | Number of Dogs (per group) |
|---|---|---|
| Example 6 | 3 | 5 |
| Example 7 | 3 | 4 |
| Example 8 | 3 | 5 |
| Crystal of Compound No. 1 | 6 | 2 |
| Comparative Example 1 | 4 | 5 |

Pharmacokinetic parameters in the results of this comparative absorbability test are shown in Table 3.

TABLE 3

| | The Area under the Plasma Concentration Curve (0 - 24, ng · h/ml) |
|---|---|
| Administrated Formulation | Intact Drug (in terms of 3 mg/kg) |
| Example 6 | 404.3 ± 80.1 |
| Example 7 | 156.2 ± 141.5 |
| Example 8 | 110.3 ± 53.6 |
| Crystal of Compound No. 1 | 69.9 ± 2.6 |
| Comparative Example 1 | 77.3 ± 61.8 |

As is revealed from the results of this comparative absorbability test, the solid dispersions of the present invention have greater absorbability than the crystal of Compound No. 1 and the dosage form of Comparative Example 1.

BEST MODE FOR CARRYING OUT THE INVENTION

EXAMPLE 1

Thirty grams of Compound No. 1 and 90 g of methacrylate copolymer L (Eudragit L100; Röhm Pharma Co., Ltd.) were dissolved in 700 g of an ethanol/methylene chloride (1/1 by weight) mixed solution, and the resultant was then sprayed on 880 g of lactose (#200 mesh) by a fluidized-bed granulating method to obtain a solid dispersion. Concerning the conditions for the fluidized-bed granulating at this time, the intake air temperature was 60° C., the solid ingredient concentration in the spray solution was 15% by weight/volume, and the spraying pressure was 2.0 kg/cm$^2$. The powder characteristics of the solid dispersion containing 3% by weight of Compound No. 1 are shown in Table 4.

TABLE 4

| Apparent Specific Volume | |
|---|---|
| Loose Specific Volume (ml/g) | 2.32 |
| Tapped Specific Volume (ml/g) | 1.75 |

EXAMPLE 2

Figure 2:
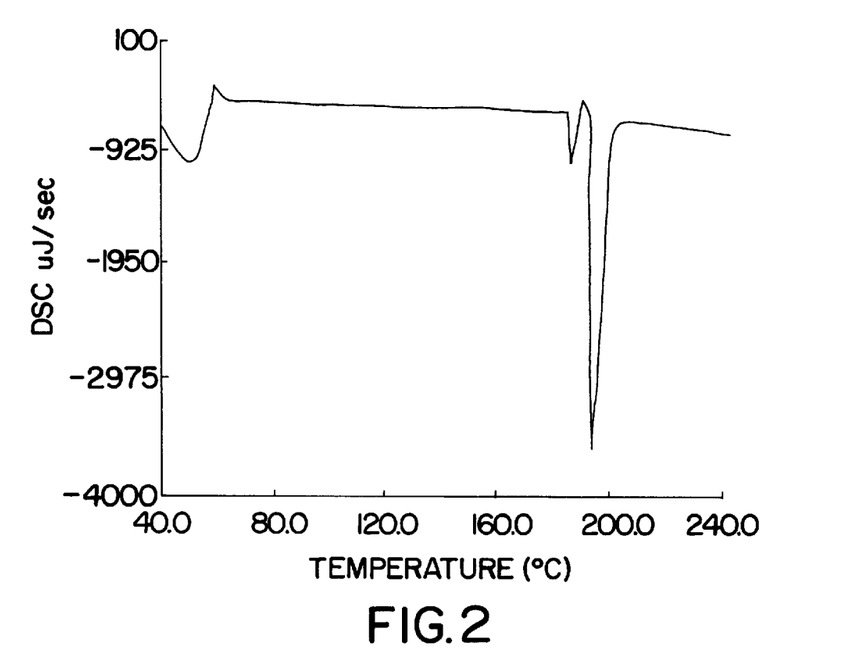
FIG. 2 shows the results of measurement by a differential scanning calorimeter (DSC) for Compound No. 1.
Figure 3:
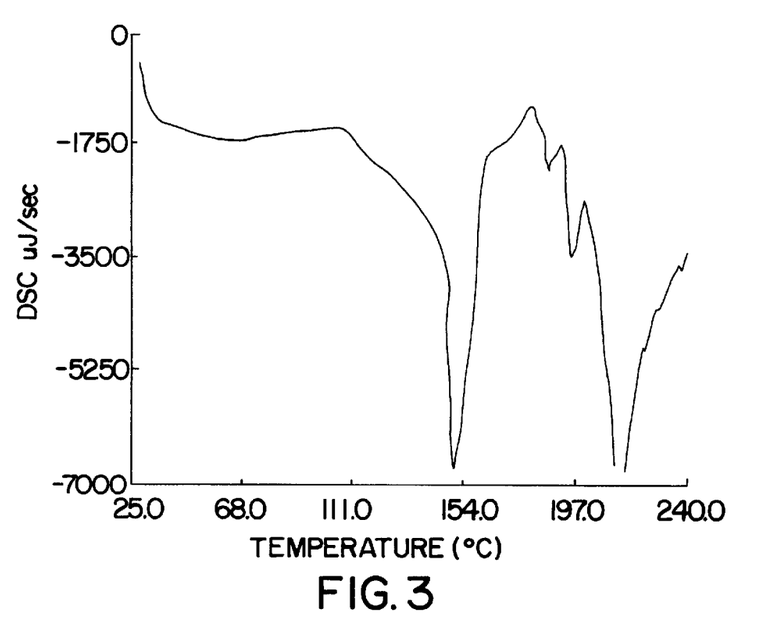
FIG. 3 shows the results of DSC measurement for a physically mixed composition according to the same recipe as the solid dispersion of Example 3.
Figure 4:
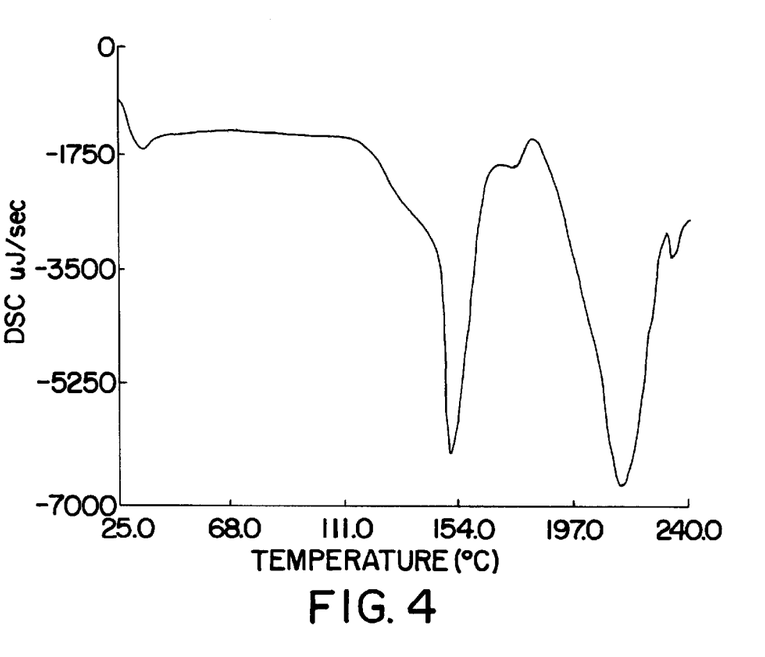
FIG. 4 shows the results of DSC measurement for the solid dispersion of Example 3.

A solid dispersion containing 20% by weight of Compound No. 1 was obtained in a manner similar to that in Example 1 except that the quantity of Compound 1 was 200 g, that of methacrylate copolymer L was 200 g, and that of lactose was 100 g. The results of DSC measurement on Compound No. 1 alone are shown in FIG. 2, those on a physically mixed composition according to the same recipe as a solid dispersion containing 20% by weight of Compound No. 1 are shown in FIG. 3, and those on a solid dispersion containing 20% by weight of Compound No. 1 are shown in FIG. 4. Since the melting point peak of Compound No. 1, which appears in FIGS. 2 and 3, disappears in FIG. 4, it is suggested that the solid dispersion according to the present invention became amorphous.

EXAMPLE 3

A solid dispersion containing 3% by weight of Compound No. 1 was obtained in a manner similar to that in Example 1 except that a water-soluble polymer, polyvinyl pyrrolidone K30, was used instead of methacrylate copolymer L.

EXAMPLE 4

Figure 5:
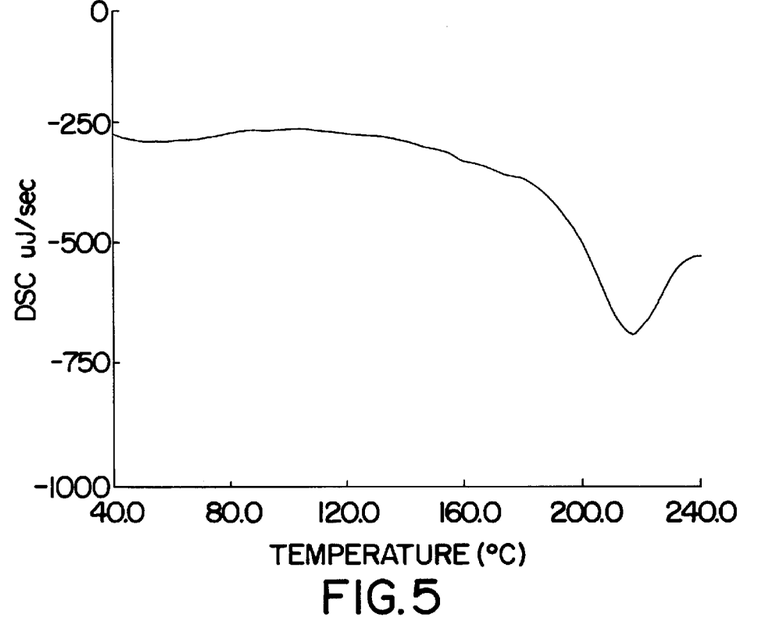
FIG. 5 shows the results of DSC measurement for the solid dispersion of Example 4.

Using a biaxial extruder (manufactured by Kurimoto, Ltd.), 75 g of Compound No. 1 and 225 g of methacrylate copolymer L (Eudragit L100; Röhm Pharma Co., Ltd.) were heat-melt-kneaded to obtain a solid dispersion in which the concentration of Compound No. 1 was 25% by weight. The results of DSC measurement on this solid dispersion are shown in FIG. 5. Since the melting point peak of Compound No. 1 disappears, it is suggested that the solid dispersion became amorphous.

EXAMPLE 5

Figure 6:
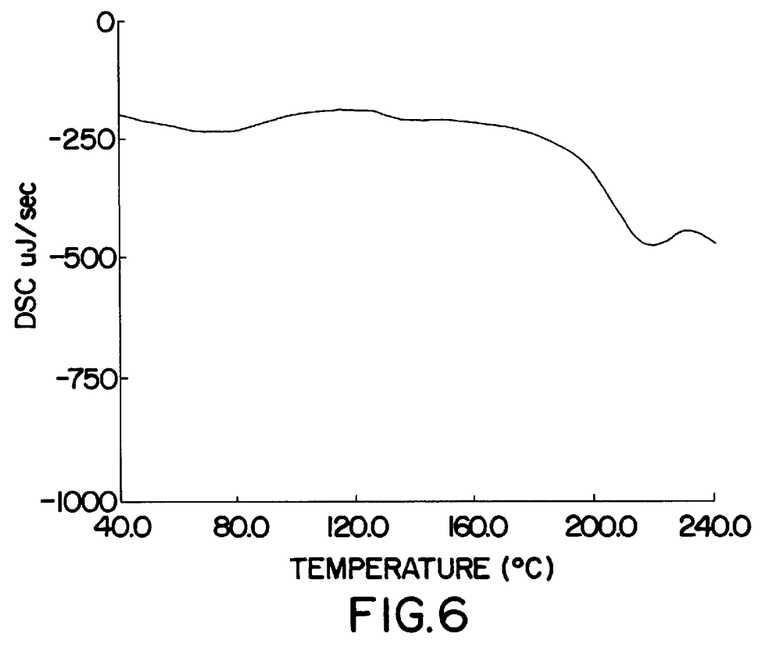
FIG. 6 shows the results of DSC measurement for the solid dispersion of Example 5.

Using a biaxial extruder (manufactured by Kurimoto, Ltd.), 150 g of Compound No. 1 and 150 g of methacrylate copolymer L (Eudragit L100; Röhm Pharma Co., Ltd.) were heat-melt-kneaded to obtain a solid dispersion in which the concentration of Compound No. 1 was 50% by weight. The results of DSC measurement on this solid dispersion are shown in FIG. 6. Since the melting point peak of Compound No. 1 disappears, it is suggested that the solid dispersion became amorphous.

EXAMPLE 6

The solid dispersion obtained in Example 1 was packed in Size 0 of gelatin hard capsules at 333.3 mg to obtain solid dispersion dosage forms each containing 10 mg of Compound No. 1.

EXAMPLE 7

The solid dispersion obtained in Example 2 was packed in Size 2 of gelatin hard capsules at 150.0 mg to obtain solid dispersion dosage forms each containing 30 mg of Compound No. 1

EXAMPLE 8

The solid dispersion obtained in Example 3 was packed in Size 0 of gelatin hard capsules at 333.3 mg to obtain solid dispersion dosage forms each containing 10 mg of Compound No. 1.

COMPARATIVE EXAMPLE 1

Forty point zero grams of a finely ground product of Compound No. 1, 137.6 g of lactose, 59.0 g of corn starch, and 13.0 g of polyvinyl pyrrolidone were fluidized-bed-granulated using a binder solution comprising 7.8 g of polyvinyl alcohol dissolved in 31.2 g of distilled water. To this granulated composition, 2.6 g of magnesium stearate was admixed to produce tablets. At this time, each tablet contained 20.0 mg of the finely ground product of Compound No. 1, 68.8 mg of lactose, 29.5 mg of corn starch, 6.5 mg of polyvinyl pyrrolidone, 3.9 mg of polyvinyl alcohol, and 1.3 mg of magnesium stearate.

INDUSTRIAL APPLICABILITY

According to the present invention, there is provided a solid dispersion or a solid dispersion dosage form of a slightly-soluble and crystalline drug, compound (I), wherein the solid dispersion or the solid dispersion dosage form has high solubility and absorbability, and also has powder characteristics suitable for production at an industrial scale.

What is claimed is:

1. A solid dispersion dosage form, comprising an amorphous xanthine derivative represented by the following formula (I) or a pharmacologically allowable salt thereof and an enteric-coating polymer:

(I)

wherein $R^1$ and $R^2$ are the same or different, and represent substituted or unsubstituted lower alkyl groups, and Q represents a hydrogen atom or a hydroxyl group, and wherein said polymer is at most 20% (w/w) of said dosage form and the amount (w/w) of said derivative present in said dosage form is no more that of said polymer.

2. The solid dispersion dosage form according to claim 1, wherein said polymer is selected from methacrylate copolymer L, hydroxypropylmethyl cellulose phthalate, hydroxypropylmethyl cellulose acetate succinate, or carboxymethylethyl cellulose.

3. A solid dispersion dosage form according to any one of claims 1 or 2, which is obtained by fluidized-bed granulation.

4. A solid dispersion dosage form according to any one of claims 1 or 2, which is obtained by heat-melt kneading.

* * * * *

UNITED STATES PATENT AND TRADEMARK OFFICE
CERTIFICATE OF CORRECTION

PATENT NO.    : 6,254,889 B1                             Page 1 of 1
DATED         : July 3, 2001
INVENTOR(S)   : Makoto Kigoshi et al.

It is certified that error appears in the above-identified patent and that said Letters Patent is hereby corrected as shown below:

Title page,
Item [56] References Cited, under U.S. PATENT DOCUMENTS, "Tsam et al." should read -- Tsan et al. --.

Column 6,
Line 41, "pf" should read -- of --; and
Line 45, "an" should read -- a --.

Column 10,
Line 19, "more that" should read -- more than that --.

Signed and Sealed this

Second Day of April, 2002

*Attest:*

JAMES E. ROGAN
*Attesting Officer*      *Director of the United States Patent and Trademark Office*

UNITED STATES PATENT AND TRADEMARK OFFICE
CERTIFICATE OF CORRECTION

PATENT NO. : 6,254,889 B1
DATED : July 3, 2001
INVENTOR(S) : Makoto Kigoshi et al.

It is certified that error appears in the above-identified patent and that said Letters Patent is hereby corrected as shown below:

Column 10,
Lines 5-10, the fomula should read as follows:

Signed and Sealed this

Fourth Day of January, 2005

JON W. DUDAS
*Director of the United States Patent and Trademark Office*